United States Patent [19]
Reznik et al.

[11] 3,948,901
[45] Apr. 6, 1976

[54] BIS (2,4-DIOXOTETRAHYDROPYRIMIDINYL-5-SULPHONOAMIDO) DIPHENYLSULPHONER

[76] Inventors: Vladimir Savich Reznik, ulitsa Gospitalnaya, 34, kv. 34; Nikolai Grigorievich Pashkurov, ulitsa Druzhby, 6, kv. 20; Abdurakhim Abdurakhimovich Muslinkin, ulitsa Zhdanova, 60, kv. 33; Nikolai Mikhailovich Smirnov, ulitsa Artilleristov, 25/38, kv. 65, all of Kazan; Nikolai Mikhailovich Goloschapov, ulitsa Druzhby, 9, kv. 110, Zagorsk, all of U.S.S.R.

[22] Filed: Apr. 22, 1974

[21] Appl. No.: 463,168

[52] U.S. Cl. .................................. 260/239.75
[51] Int. Cl.² .................................. C07D 239/44
[58] Field of Search .................... 260/239.75

[56] References Cited
FOREIGN PATENTS OR APPLICATIONS
1,459,732   3/1962   France ................ 260/239.75

OTHER PUBLICATIONS
Chem. Abst. 59, 9898 (h) (1963) Timmler et al. "Halogen–Containing Sulfones".

*Primary Examiner*—Jerome D. Goldberg
*Assistant Examiner*—D. W. Robinson
*Attorney, Agent, or Firm*—Holman & Stern

[57] ABSTRACT

ω,ω' -bis(2,4-dioxotetrahydropyrimidinyl-5-sulphonoamido)diarylsulphones having the general formula

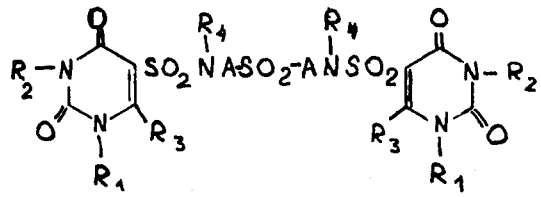

where $R_1$, $R_2$, $R_3$, $R_4$ are hydrogen or at least one of the $R_1$, $R_2$, $R_3$, $R_4$ is alkyl if A is phenylene.

The method for preparing ω,ω' bis(2,4-dioxotetrahydropyrimidinyl-5-sulphonoamido)-diaryl- and -dialkylsulphones comprising reacting sulphochlorides having the general formula

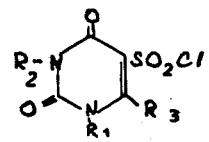

where $R_1$, $R_2$, and $R_3$ are hydrogen, or at least one of them is alkyl, with ω,ω'-diaminodiaryl- or -dialkylsulphones having the general formula

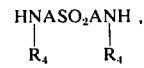

where $R_4$ is hydrogen or alkyl, A is phenylene or alkylene, in an organic solvent medium in the presence of an organic base which binds the evolving hydrogen chloride, at a temperature of from 20°– 100°C, and finally isolating the end product.

5 Claims, No Drawings

BIS (2,4-DIOXOTETRAHYDROPYRIMIDINYL-5-SULPHONOAMIDO) DIPHENYLSULPHONER

This invention relates new substances, namely, ω,ω'-bis (2,4-dioxotetrahydropyriminidyl-5-sulphonoamido)diaryl- and -dialkylsulphones and the method for preparing same.

According to the invention, said novel substances are characterized by the following general formula:

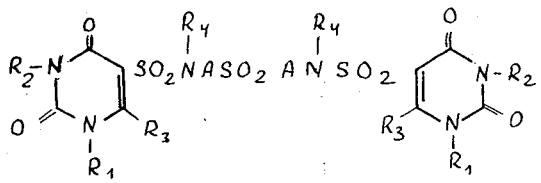

where $R_1$, $R_2$, $R_3$ and $R_4$ are hydrogen, or at least one of $R_1$, $R_2$, $R_3$, $R_4$ is alkyl if A is phenylene and if A is alkylene then $R_1$, $R_2$, $R_4$ are hydrogen and $R_3$ is alkyl.

The proposed compounds are white or slightly yellowish crystalline substances decomposing at temperatures above 130°C, are moderately soluble in water, dimethylsulphoxide, and in warm dimethylformamide; are practically insoluble in benzene, ether and chloroform; are decomposed by alkalies and concentrated mineral acids; and the aqueous solutions of the proposed substances are slowly decomposed in storage.

Said substances are pharmacologically active and can therefore be used in medicine. Moreover they can be used as model compounds or clarification of the action of some medicinal preparations for example, antileprotic preparations, viz., diaphenylsulphone (DDC, Avlosulfon, Dapsone, Sulfonmere, and others), solusulphone (Cimedone, Novotrone, Solasulfonum and others), and sulphapyridazine (Sulfamethoxypyridarine) and others.

The most characteristic representatives of the said compounds according to the invention have the following formulas: 4,4-bis(2,4-dioxo-1,2,3,4-tetrahydropyrimidinyl-5sulphonoamido)diphenylsulphone

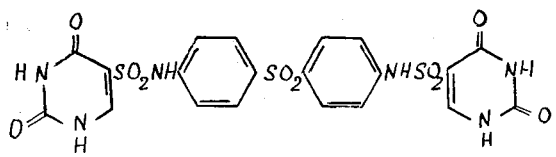

4,4-bis[2,4-dioxo-6-methyl-1,2,3,4-tetrahydropyrimidinyl-5-sulphono(N-methyl)amido]diphenylsulphone

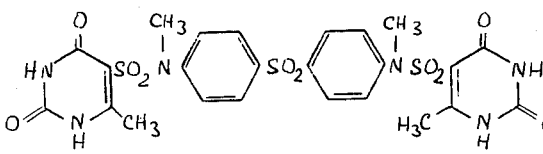

4,4-bis[2,4-dioxo-6-methyl-1,2,3,4-tetrahydropyrimidinyl-5-sulphono(N-n-butyl)amido]diphenylsulphone

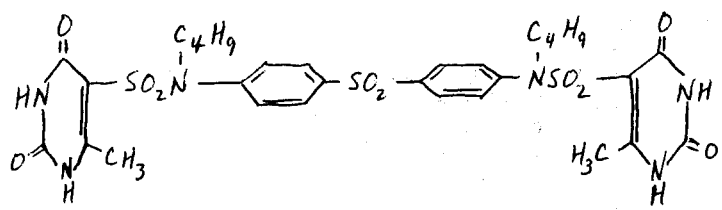

4,4-bis(2,4-dioxo-3,6-dimethyl-1,2,3,4-tetrahydropyrimidinyl-5-sulphonoamido)diphenylsulphone

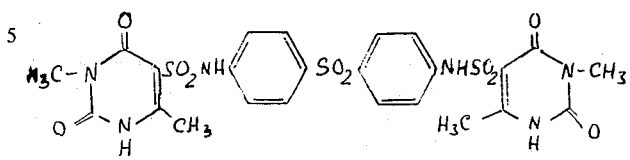

and β,β'-bis(2,4-dioxo-6-methyl-1,2,3,4-tetrahydropyrimidinyl-5-sulphonoamido)diethylsulphone.

The experimental studies of the antileprotic activity of the preparation were carried out with 4,4'-bis(2,4-dioxo-1,2,3,4-tetrahydropyrimidinyl-5-sulphonoamido)diphenylsulphone and 4,4'-bis[(2,4-dioxo-6-methyl-1,2,3,4-tetrahydropyrimidinyl-5-sulphono(N-methyl)amido]diphenylsulphone.

The experiments were carried out as follows:

BALB/c line mice were infected subcutaneously in the right groin with strain 166 bacteria isolated from mice that had been inoculated with human leproma material by the Shephard method and which subsisted by passage through mice. An overdose of the infecting bacteria were introduced and subcutaneous granulomas (lepromas) developed at the site of the infection in 100 per cent mice by the third month following the infection.

Each preparation was tested on twenty mice. The control group of mice, also 20, received no treatment.

The proposed preparation was administered to the infected mice with food in the quantity of 10 mg daily per mice weighing 18–20 g. The preparation was administered immediately after infection and the therapy continued for three months.

The results of the experiment show that the greatest antileprotic activity is inherent in the preparation 4,4-bis(2,4-dioxo-1,2,3,4-tetrahydropyrimidinyl-5-sulphonoamido)diphenylsulphone.

The toxicity of the above compounds, when tested on albino mice, had an $LD_{50}$ of from 800-2500 mg per kg body weight (peroral administration).

The method for preparing the above new compounds ω,ω'-bis(2,4-dioxotetrahydropyrimidinyl-5-sulphonoamido)diaryl- and -dialkylsulphones, according to the invention, consists in that sulphochlorides having the general formula

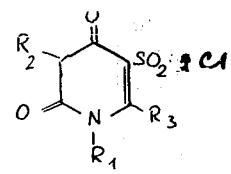

where $R_1$, $R_2$, $R_3$ are hydrogen, or at least one of the $R_1$, $R_2$, $R_3$ is alkyl, are reacted with ω,ω'-diaminodiaryl- or -dialkylsulphones having the general formula

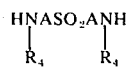

where $R_4$ is hydrogen or alkyl, where A is phenylene or alkylene, in a medium of an organic solvent in the presence of an organic base that bonds the envolving hydrogen chloride, at at temperature of from 20-100°C and, finally the end product is isolated. In order to increase the yield and to improve the quality of the end product, the starting substances are taken a stoichiometric ratio.

It is recommended to use dimethylformamide or butylacetate, or else, dimethylsulphoxide as the organic solvents. It is also recommended to use triethylamine N,N-diethylaniline or pyridine as the organic bases bonding hydrogen chloride.

The proposed method can be realized as follows. ω,ω'-diaminodiaryl- or dialkylsulphones having the general formula

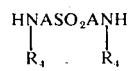

where $R_4$ is hydrogen or alkyl, where A is phenylene, alkylene, are mixed with an organic base, preferably with triethyleneimine, N,N-diethylaniline or pyridine, in a medium of an organic solvent, for example, dimethylformamide, butylacetate or dimethylsulphoxide.

A sulphochloride having the general formula

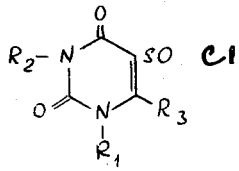

where $R_1$, $R_2$, $R_3$ are hydrogen or at least one of $R_1$, $R_2$, $R_3$ is alkyl is added to the mixture.

The process is carried out at a temperature of from 20°-100°C. The end product is isolated by known methods. The yield of the end product is up to 75 percent of theory.

For a better understanding of the invention, the following examples of its practical embodiment are given by way of illustration.

EXAMPLE 1

A solution of 11 g (0.045 M) of 4,4'-diaminodiphenyl-sulphone and 13 ml of triethylamine in 125 ml of anhydrous dimethylformamide are combined with stirring at a temperature of 45°-55°C, with 19 g (0.09 M) of uracyl-5-sulphochloride, and the mixture is heated for 90 minutes at a temperature of 55°-60°C. The reaction mixture is cooled, whereupon the precipitated crystals are separated on a filter, washed with chloroform and ethyl alcohol, and then dried. The yield of 4,4'-bis(2,4-dioxo-1,2,3,4-tetrahydropyrimidinyl-5-sulphonoamido)diphenylsulphone is 19 g (72 per cent of theory). After recrystallization from dimethylformamide and water, the product is a colourless crystalline substance melting with decomposition at a temperature of from 239°-242°C.

Calculated for $C_{20}H_{16}N_6O_{10}S_3$, in per cent by weight: C 40.27; H 2.68; N 1409. Found, in per cent by weight C 4080; H 3.01; N 14.25.

EXAMPLE 2

A solution of 22 g (0.09 M) of 4,4'-diaminodiphenyl-sulphone and 25 ml of triethylamine in 130 ml of anhydrous dimethylformamide are combined with stirring at room temperature, with 43 g (0.18 M) of 2,4-dioxo-3,6-dimethyl-1,2,3,4-tetrahydropyrimidinyl-5-sulphochloride. The mixture is cooled by an external source in order to maintain the temperature within a range of from 50°-55°C. The mixture is then heated for 90 minutes at a temperature of 55°-60°C, then cooled and poured into 0.5 liter of sulphuric ether. The oily product is mixed with ether, the ether is then decanted, and the product is treated with several portions of chloroform. The product crystallizes gradually and then turns into powder. It is recrystallized from a mixture of ethyl alcohol and dimethylformamide. The product is pale yellow crystals which are decomposed at temperatures above 170°C. The yield of 4,4'-bis(2,4-dioxo-3,6-dimethyl-1,2,3,4-tetrahydropyrimidinyl-5-sulphonoamido)diphenylsulphone is 29.5 g, which is 51 per cent by weight of theory.

Calculated for $C_{24}H_{24}N_6O_{10}S_3$ in per cent by weight are: C 44.17; H 3.68; N 1288. Found, in per cent by weight are: C 44.48; H 3.92; N 12.71.

EXAMPLE 3

A solution of 12.4 g (0.045 M) of bis(4,4'-methylaminophenyl)sulphone and 25 ml of triethylamine in 200 ml of anhydrous dimethylformamide are combined, with stirring at a temperature of 30°C, with 21.5 g (0.09 M) of 6-methyluracyl-5-sulphochloride, and the mixture is heated for thirty minutes at a temperature of from 80°-95°C. The cooled mass is discharged into chloroform. The precipitate is separated on a filter, washed with chloroform and ethyl alcohol. After recrystallization from dimethylformamide, the yield of 4,4'-bis[2,4-dioxo-6-methyl1,2,3,4-tetrahydropyrimidinyl-5-sulphono(N-methyl)amino]diphenylsulphone is 9.2 g, which is 28.2 per cent by weight of theory. The product is a white crystalline substance melting with decomposition at a temperature from 210° to 240°C (depending on the rate of heating).

Calculated for $C_{24}H_{24}N_6O_{10}S_3$, in per cent by weight are: C 44.17; H 3.68; N 12.88. Found in per cent by weight are: C 44.53; H 3.75; N 13.21.

EXAMPLE 4

A solution of 11 g (0.045 M) of 4,4'-diamino-diphenylsulphone and 14.3 g of N,N-diethylamiline in 125 ml of anhydrous dimethylformamide are combined, with stirring at a temperature of from 45°-55°C, with 19 g (0.09 M) of uracyl-5-sulphochloride, and the mass is heated for 90 minutes at a temperature of 55°-60°C. The end product is isolated by a procedure similar to that described in Example 1. The yield of 4,4'-bis(2,4-dioxo-1,2,3,4-tetrahydropyrimidinyl-5-sulphonoamido)diphenylsulphone is 18 g, which is 69 per cent by weight of theory.

EXAMPLE 5

A solution of 11 g (0.045 M) of 4,4'-diaminodiphenylsulphone and 8 ml of pyridine in 125 ml of anhydrous dimethylformamide are combined, with stirring at a temperature of 45°-55°C with 19 g (0.09 M) of uracyl-5-sulphochloride. The process is carried out as described in Example 1. The yield of the product is 13.5 g (52 per cent by weight of theory). The isolation procedure is the same as in Example 1.

EXAMPLE 6

A solution of 11 g (0.045 M) of 4,4'-diaminodiphenylsulphone and 13 ml of triethylamine in 250 ml of butyl acetate are combined, with stirring at a temperature of 45°–55°C, with 19 g (0.09 M) of uracyl-5-sulphochloride and the mass is heated for 90 minutes at a temperature of 55°–60°C. The reaction mixture is then cooled, poured into 1 liter of diethyl ether, whereupon the precipitate is separated from the solution and processed with hot chloroform in order to convert the precipitate into powder. The precipitate is separated on a filter, washed with chloroform, ethyl alcohol, and then dried. The yield of 4,4'-bis(2,4-dioxo-1,2,3,4-tetrahydropyridiminyl-5-sulphonoamido)diphenylsulphone is 11.2 g, which is 43 per cent by weight of theory.

Calculated, in per cent by weight are: C 40.27; H 2.68; N 14.09. Found, in per cent by weight are: C 40.80; H 3.01; N 14.25.

EXAMPLE 7

A solution of 11 g (0.045 M) of 4,4'-diaminodiphenylsulphone and 13 ml of triethylamine in 100 ml of anhydrous dimethylsulphoxide are combined, at a temperature of from 45°–55°C. while stirring with 19 g (0.09 M) of uracyl-5-sulphochloride. The procedure is similar to that described in Example 6. The yield of the end product is 7.8 g, which is 30 per cent by weight of theory.

EXAMPLE 8

A solution of 10 g (0.03 M) of N,N-dibutylaminodiphenylsulphone and 12.5 g (0.06 M) of 6-methyluracyl-5-sulphochloride in absolute dimethylformamide are combined, slowly with stirring at a temperature of 30°–35°C, with a solution of 8.4 g (0.06 M) of N,N-diethylaniline in 20 ml of dimethylformamide. As soon as the entire quantity of the diethylaniline solution is added, the temperature of the mixture is raised gradually to 70°–75°C and the mixture is kept at this temperature for three hours. The mixture is then cooled and poured into ether, whereupon the oily layer is washed several times with cold chloroform. The oil converts into a powder which is separated on a filter, washed with chloroform, and boiled in 50 ml of anhydrous methyl alcohol. Then precipitate is separated on a filter while hot, then dissolved in hot dimethylformamide (90°–100°C), where the solution is passed through a filter and the product is precipitated by adding slowly a mixture of methyl alcohol and ether (1:1). The white crystalline precipitate is separated on a filter, washed with methyl alcohol, ether, and then dried. The yield of ω,ω'-bis[2,4-dioxo-6-methyl-1,2,3,4-tetrahydropyrimidinyl-5-sulphono (N,n-butylamido)]diphenylsulphone is 5.3 g, which is 26 per cent by weight of theory. The product is decomposed with heating at temperatures of 181°–183°C.

Calculated, in per cent by weight are: N 11.40; for $C_{30}H_{36}N_6O_{10}S_3$.

Found, in per cent by weight are: N 11.22; 11.19.

EXAMPLE 9

A solution of β,β'-diaminodiethylsulphone, prepared by reacting 10 g (0.004 M) of β,β'-diaminodiethylsulphonedihydrochloride with 2.1 g of sodium hydride in dimethylformamide are combined, at a temperature of 20°–25°C, with 20 g (0.008M) of 6-methyluracyl-5-sulphochloride, and then, with gradual stirring a solution of 9.1 g (0.088 M) of triethylamine in 10 of dimethylformamide is added. The mixture is then stirred for 3 hours at a temperature of 20°–25°C and for 1 hour at a temperature of 80°–85°C. The mixture is cooled, poured into ether, whereupon the oil formed is treated with 200 ml of dry acetone, and the acetone extract is then filtered and allowed to stand. Colourless crystals of β,β'-bis(2,4-dioxo-6-methyl-1,2,3,4-tetrahydropyrimidinyl-5-sulphonoamido)diethylsulphone are gradually precipitated from the solution. The yield of the product is 3.2 g, which is 14 per cent of theory. The product melts with decomposition at a temperature from 231° to 235°C.

Calculated, in per cent by weight are: N 15.9, for $C_{14}H_{20}N_6O_{10}S_3$.

Found, in per cent by weight are: N 15.47; 15.52.

What is claimed is:

1. ω,ω'-bis(2,4-dioxotetrahydropyrimidinyl-5-sulphonoamido) diphenylsulphones having the general formula:

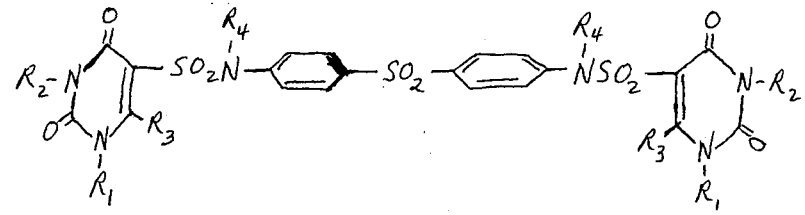

wherein $R_1$, $R_2$, $R_3$ and $R_4$ are hydrogen or lower alkyl.

2. The diphenylsulphone, 4,4'-bis[2,4-dioxo-6-methyl-1,2,3,4-tetrahydropyrimidinyl-5-sulphono(N-n-butyl)amido] diphenylsulphone, as claimed in claim 1 having the following formula:

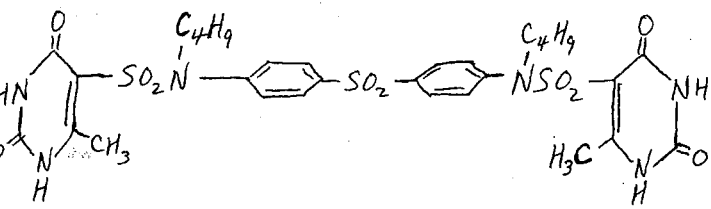

3. The diphenylsulphone, 4,4'-bis(2,4-dioxo-1,2,3,4-tetrahydropyrimidinyl-5-sulphonoamido)diphenylsulphone, as claimed in claim 1 having the following formula:

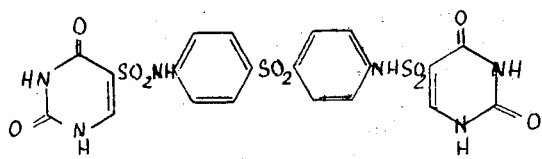
4. The diphenylsulphone, 4,4'-bis](2,4-dioxo-6-methyl-1,2,3,4-tetrahydropyrimidinyl-5-sulphono(N-methyl)amido]diphenyl-sulphone, as claimed in claim 1, having the following formula:
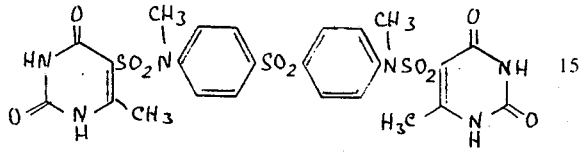
5. The diphenylsulphone, 4,4'-bis(2,4-dioxo-3,6-dimethyl-1,2,3,4tetrahydropyrimidinyl-5-sulphonoamido)diphenylsulphone, as claimed in claim 1 having the following formula:
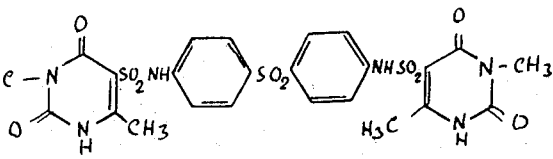
* * * * *